US007626076B2

(12) United States Patent
Shin et al.

(10) Patent No.: US 7,626,076 B2
(45) Date of Patent: Dec. 1, 2009

(54) TRANSGENIC MOUSE WHOSE GENOME COMPRISES A HOMOZYGOUS DISRUPTION OF ITS α1G GENE, A METHOD OF PREPARING THE SAME AND USE THEREOF

(75) Inventors: Hee-Sup Shin, Uiwang-si (KR); Daesoo Kim, Seoul (KR); Sehoon Keum, Seoul (KR); Inseon Song, Kunpo-si (KR)

(73) Assignee: Orient Bio., Inc. (KR)

( * ) Notice: Subject to any disclaimer, the term of this patent is extended or adjusted under 35 U.S.C. 154(b) by 0 days.

(21) Appl. No.: 11/986,671

(22) Filed: Nov. 23, 2007

(65) Prior Publication Data

US 2008/0201787 A1 Aug. 21, 2008

Related U.S. Application Data

(63) Continuation-in-part of application No. 10/493,376, filed as application No. PCT/KR02/00087 on Jan. 18, 2002, now abandoned.

(51) Int. Cl.
*A01K 67/027* (2006.01)
*G01N 33/00* (2006.01)
*C12N 15/00* (2006.01)

(52) U.S. Cl. .............................. 800/18; 800/3; 800/21
(58) Field of Classification Search .................... 800/18, 800/3, 21
See application file for complete search history.

(56) References Cited

U.S. PATENT DOCUMENTS

2006/0025397 A1 2/2006 Shin et al.

OTHER PUBLICATIONS

Sohal (Neuron, 2001, 31: p. 3-4.*
Kim, Neuron, 2001, 31: 35-45.*
MGI webpage labeled "Mammalian Phenotype Browser" for seizures, 2008.*
Schoonjans (Stem Cells, 2003, vol. 21, p. 90-97).*
Wolfer (Trends in Neuroscience, 2002, 25(7): 336-340).*
Strunk (Genetics, 2004, vol. 167, p. 1821-1832).*
Schauwecker (Progress in Brain Research, 002, 135: 139-148).*
Scarff (genesis, 2003, vol. 36, p. 149-154).*
Agueev et al., "Low Affinity Block of the T-Type Alpha1G Ca2+ Channel by the Anti-Epileptic Drug Gabapentin," *Biophys. J.* 78:457A, 2000. (Abstract).
Kim et al., "Lack of the Burst Firing of Thalamocortical Relay Neuorons and Resistance to Absence Seizures in Mice Lacking $α_{1G}$ T-type $Ca^{2+}$ Channels," *Neuron.* 31:35-45, 2001.

Lacinová et al., "Regulation of the Calcium Channel $α_{1G}$ Subunit by Divalent Cations and Organic Blockers," *Neuropharmacology* 39:1254-1266, 2000.
Monteil et al., "Molecular and Functional Properties of the Human $α_{1G}$ Subunit That Forms T-type Calcium Channels," *J. Biol. Chem.* 275:6090-6100, 2000.
Perez-Reyes, "Molecular Characterization of a Novel Family of Low Voltage-Activated, T-Type, Calcium Channels," *J. Bioenerg. Biomembr.* 30:313-318, 1998.
Schauwecker, "Complications Associated with Genetic Background Effects in Models of Experimental Epilepsy," *Prog. Brain Res.* 135:139-148, 2002.
Schoonjans et al., Improved Generation of Germline-Competent Embryonic Stem Cell Lines from Inbred Mouse Strains, *Stem Cells* 21:90-97, 2003.
Sohal and Huguenard, "It Takes T to Tango," *Neuron.* 31:3-4, 2001.
Song et al., "Role of T-type Channels in the Genesis of Absence Seizure in the Mutant Mice for α1A, the Pore-forming Subunit of the P/Q-type Calcium Channel," $31^{st}$ Annual Meeting of the Society for Neuroscience San Diego, California, vol. 27, No. 1, p. 397, Nov. 10-15, 2001 (Abstract).
Strunk et al., "Phenotypic Variation Resulting From a Deficiency of Epidermal Growth Factor Receptor in Mice is Caused by Extensive Genetic Heterogeneity That Can Be Genetically and Molecularly Partitioned," *Genetics 167*:1821-1832, 2004.
Takeda et al., "Left-Right Asymmetry and Kinesin Superfamily Protein KIF3A: New Insights in Determination of Laterality and Mesoderm Induction by $kif3A^{-/-}$ Mice Analysis," *J. Cell. Biol.* 145:825-826, 1999.
Talley et al., "Low-Voltage-Activated Calcium Channel Subunit Expression in a Genetic Model of Absence Epilepsy in the Rat," *Mol. Brain Res.* 75:159-165, 2000.
Wolfer et al., "Knockout Mice: Simple Solutions to the Problems of Genetic Background and Flanking Genes," *Trends Neurosci.* 25:336-340, 2002.

* cited by examiner

*Primary Examiner*—Michael C. Wilson
(74) *Attorney, Agent, or Firm*—Klarquist Sparkman, LLP (57) ABSTRACT

The disclosure concerns a method for resistance of epilepsy by suppressing the function of alpha 1G protein of T-type calcium channels, use of suppressor of alpha 1G protein for prevention or treatment for epilepsy, knockout mice resisting epilepsy by disrupting alpha 1G subunit of T-type calcium channel, and preparation method thereof. The α1G-knockout transgenic mouse can be used for investigating the relationship between diseases particularly neuropathy or psychopathy and the function of α1G T-type calcium channel via various behavioral tests since α1G subunit is mainly expression in central nervous system (CNS) and pheripheral nervous system (PNS). Further, the α1G-knockout transgenic mouse can be used for screening antileptic agents.

10 Claims, 10 Drawing Sheets

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: F1 primer

<400> SEQUENCE: 1
atacgtggtt cgagcgagtc                                               20

<210> SEQ ID NO 2
<211> LENGTH: 20
<212> TYPE: DNA
<213> ORGANISM: Artificial
<220> FEATURE:
<223> OTHER INFORMATION: B1 primer

<400> SEQUENCE: 2
cgaaggcctg acgtagaaag                                               20

<210> SEQ ID NO 3
<211> LENGTH: 22
<212> TYPE: DNA
<213> ORGANISM: Artificial
<220> FEATURE:
<223> OTHER INFORMATION: PGK22

<400> SEQUENCE: 3
ctgactaggg gaggagtaga ag                                            22

<210> SEQ ID NO 4
<211> LENGTH: 12
<212> TYPE: PRT
<213> ORGANISM: Artificial
<220> FEATURE:
<223> OTHER INFORMATION: anti-alpha1G Ab epitope

<400> SEQUENCE: 4

Cys Asn Gly Lys Ser Ala Ser Gly Arg Leu Ala Arg
1               5                   10
```

TRANSGENIC MOUSE WHOSE GENOME COMPRISES A HOMOZYGOUS DISRUPTION OF ITS α1G GENE, A METHOD OF PREPARING THE SAME AND USE THEREOF

CROSS-REFERENCE TO RELATED APPLICATIONS

This is a continuation-in-part of U.S. patent application Ser. No. 10/493,376, filed Apr. 23, 2004, now abandoned which is the U.S. National Stage of International Application No. PCT/KR2002/000087, filed Jan. 18, 2002, which in turn claims priority to Korean Patent Application No. 2001-0066257, filed Oct. 26, 2001.

FIELD OF THE INVENTION

The present invention relates to a method for resisting epilepsy by suppressing the function of the alpha 1G (α1G) protein in T-type calcium ($Ca^{2+}$) channels, a use of a suppressor of the α1G protein for the prevention and treatment of epilepsy, a knockout mouse resisting epilepsy by disrupting α1G subunit of T-type calcium channels, a preparation method of the knockout mouse and use thereof.

BACKGROUND OF THE INVENTION

Epilepsy is a nervous disorder accompanied by chronic or recurring seizures, which are essentially abnormal brain waves resulting from an abnormal depolarization of brain cells. Epilepsy is caused by malfunction of nervous cells of the brain due to a variety of reasons. Everyone is susceptible.

One out of every 200 people is an epilepsy patient who needs continuous treatment. Epilepsy patients in Korea total an estimated 300,000, with 30,000 new cases reported each year. The occurrence of epilepsy varies with gender and age. Epilepsy occurs more frequently in males than in females, and 75% of patients are attacked by the disease before the age of twenty, and the period from birth to four years of age shows the highest 30% of development of the disease. The rate of incidence is lower after the age of twenty but increases again after the age of sixty.

The seizures differ from person to person. Depending on where the seizure occurs, there are two basic types: generalized seizures and partial (or focal) seizures. A generalized seizure occurs on both sides of the brain, while a partial seizure occurs in a restricted area of the brain.

Partial seizures occur when brain waves start to explode abnormally in a portion of the brain cortex or cerebral hemisphere. Partial seizures can be categorized according to the state of consciousness during convulsions: (1) simple partial seizures, which occur while the patient remains conscious, (2) complex partial seizures, which occur while patients are unconscious, and (3) partial seizures evolving to secondarily generalized seizures.

Generalized seizures occur when brain waves start to explode abnormally on both sides of the brain at once and are categorized according to brain wave activity and seizure characteristics. Absence seizures (or small seizures) cause temporary loss of consciousness and exhibit symptoms such as vacant stares or rapid blinking of the eyes. Tonic-clonic seizures (or large seizures) are characterized by a stiffening of the whole body accompanied by a temporary lose of consciousness and may occur as repeated episodes. Myoclonic seizures exhibit symptoms of brief, shock-like jerks of a muscle group or groups. Atonic seizures (or small movement seizures) have symptoms of sudden exhaustion, to the point of falling down or merely a brief dropping of the head.

Complex partial seizures constitute 36% of epileptic seizures, generalized seizures constitute 23%, simple partial seizures constitute 14%, and the remainder (27%) are unidentified or unclassified.

For the treatment of epilepsy, anti-seizure medicines have been used. Most anti-seizure medicines, however, have side effects, which cause problems in blood vessels or organs. Since the mechanisms of seizures have yet to be fully explained, the treatment of epilepsy is still difficult and limited. Thus, for the development of an effective epilepsy treatment agent, it is important to gain a sufficient understanding of the seizure mechanism.

Absence seizures are characterized by a brief loss of consciousness associated with an electroencephalographic recording of 3 Hz bilaterally synchronous spike-and-wave discharges (SWDs) (Niedermeyer, *Clinical Electroencephalography*, 1996, 27, 1-21; Willams, *Brain*, 1950, 67, 50-69). Although earlier studies indicated that thalamic neurons were involved in the genesis of SWDs, more recent experiments demonstrate that the neocortex is the minimal substrate for the generation of SWDs (Steriade and Contreras, *Journal of Neurophysiology*, 1998, 80, 1439-1455; Avoli and Gloor, *Epilepsia*, 1981, 22, 443-452; Pellegrini et al., *Experimental Neurology*, 1979, 64, 155-173). Gamma-butyrolactone, (RS)-baclofen, and bicucullinemethobromide (BMB) are known to evoke absence seizures by inducing SWDs, and 4-aminopyridine (4-AP) is known to induce tonic-clonic seizures.

A series of pharmacological studies suggest that $GABA_B$ receptors play a critical role in the genesis of SWDs (Crunelli and Leresche, *Trends in Neurosciences*, 1991, 14, 16-21). It is known that $GABA_B$ receptor agonists exacerbate seizures, whereas $GABA_B$ receptor antagonists suppress seizures (Hosford et al., *Science*, 1992, 257, 393-401; Smith and Fisher, *Brain Research*, 1996, 729, 147-150; Snead, *European Journal of Pharmacology*, 1992, 213, 343-349). The anti-absence drug clonazepam is thought to act by diminishing $GABA_B$-mediated inhibitory postsynaptic potentials (IPSPs) in thalamocortical relay (TC) neurons (Gibbs et al., *Journal of Neurophysiology*, 1996, 76, 2568-79; Huguenare and Prince, 1994). The hyperpolarization of membrane potentials induced by the activation of $GABA_B$ receptors evokes rebound burst discharges in TC neurons (Crunelli and Leresche, *Trends in Neuroscience*, 1991, 14, 16-21; McCormick and Bal, *Current Opinion in Neurobiology*, 1994, 4, 550-56). This characteristic firing pattern of TC neurons is evolved by low-threshold calcium potentials (LTCPs). Therefore, it has been proposed that low-threshold T-type calcium channels are involved in the genesis of absence seizures in the thalamocortical network (Coulter et al., *Annals of Neurology*, 1989, 25, 582-593; Crunelli and Leresche, *Trends in Neuroscience*, 1991, 14, 16-21). It has been supported by a belief that drugs effective in the treatment of absence seizures, such as ethosuximide, exert their anti-absence actions through reducing T-type calcium current ($I_T$) in thalamic neurons (Coulter et al., *Annals of Neurology*, 1989, 25, 582-593; Kostyuk et al., *Neuroscience*, 1992, 51, 755-758). In addition, T-type calcium channels were moderately increased in the thalamic neurons of genetic absence epilepsy rats from Strasbourg, a model of spontaneous absence epilepsy (Talley et al., *Molecular Brain Research*, 2000, 75, 159-165; Tsakiridou et al., *Journal of Neuroscience*, 1995, 15, 3110-7).

Results from recent studies, however, have led to controversy about the role of $I_T$ in the genesis of absence seizures. For example, it was shown that ethosuximide failed to suppress $I_T$, but instead affected other channels such as noninactivating Na+ channels and Ca$^{2+}$-activated channels in TC neurons (Leresche et al., *Journal of Neuroscience*, 1998, 18, 4842-4853). Another controversy arose from the observation that, in the intracellular recording of TC neurons in vivo, the majority of neurons underwent rhythmic sequences of IPSPs and steady hyperpolarization instead of LTCPs during SWDs (Pinault et al., *Journal of Physiology (London)*, 1998, 509, 449-456). Therefore, it is not clear whether T-type calcium channels are involved in the generation of SWDs.

Thus, the present inventors have studied whether T-type calcium channels in TC neurons are directly related to the generation of absence seizures inducing SWDs, and it is proved that absence seizures do not occur in the transgenic mice who have lost the function of α1G protein, an ingredient of T-type calcium channels. The present invention has been accomplished by confirming that the inhibition of the α1G protein prevents the development of epilepsy.

SUMMARY OF THE INVENTION

It is an object of the present invention to provide a method for resisting epilepsy by suppressing the function of the α1G protein in T-type calcium (Ca$^{2+}$) channels.

It is another object of the present invention to provide a use of the α1G protein suppressor for the prevention and treatment of epilepsy.

It is a further object of the present invention to provide a transgenic mouse whose genome comprises a homozygous disruption of its α1G gene, wherein the transgenic mouse do not express α1G protein and is resistant to absence seizure.

It is also an object of the present invention to provide a preparation method of the α1G-knockout mouse.

It is also an object of the present invention to provide a method for screening antileptic agent.

DETAILED DESCRIPTION OF PREFERRED EMBODIMENTS

The present invention provides a method for resisting epilepsy by suppressing the function of the α1G protein in T-type calcium (Ca$^{2+}$) channels.

The present invention also provides a use of the α1G protein suppressor for the prevention and treatment of epilepsy.

The present invention also provides an α1G-knockout mouse, wherein the function of the α1G protein is made deficient by gene targeting.

The present invention also provides a preparation method of the α1G-knockout mouse.

Hereinafter, the present invention is described in detail.

In one aspect, the present invention provides a method for resisting epilepsy by suppressing the function of the α1G protein in T-type calcium channels.

In a preferred embodiment of the present invention, α1G transgenic mice were generated by gene targeting to disclose the function of α1G protein of T-type calcium channels. Gene targeting is a study method to determine the original function of a destroyed gene by observing pathological phenomena of an object which has that destroyed gene after disrupting a certain gene in genome by introducing a targeting vector into the gene.

The present inventors generated transgenic mice whose α1G protein was defunctionized by deleting parts of the α1G gene which is encoding a pore-forming subunit of T-type calcium channels, in order to study the mechanism of seizures using thereof.

Alpha 1G protein is a pore-forming subunit of T-type calcium channels. It is dominantly expressed in TC neurons but, significantly, is not expressed in thalamic reticular (nRT) neurons (Talley et al., *Journal of Neuroscience*, 1999, 19, 1895-1911; Talley et al., *Molecular Brain Research*, 2000, 75, 159-165). The role of α1G in vivo, however, has not been disclosed yet.

Thus, in order to clarify the role of α1G of T-type calcium channels, the present inventors have prepared α1G-deficient transgenic mice by using a common mouse strain widely used for the study of mutation based on gene targeting and for the production of transgenic animals. The transgenic mice of the present invention are homozygotes, which have α1G −/− genotype. The α1G −/− mice grew normally, and both male and female were fertile when bred with wild-type mice. All major cytoarchitectonic divisions in the thalamus, cortex, and cerebellum, which express the α1G gene, were unchanged. In addition, there were no significant histological defects in organs (e.g., heart, pancreas, intestine, liver, and kidney) obtained from the thus-produced mice.

In wild-type TC neurons, low-voltage-activated calcium ($Ca^{2+}$) currents were evoked by changing holding potentials. In contrast, calcium currents were completely absent in the TC neurons of the α1G −/− mice of the present invention, suggesting that α1G is the major component of the r-type calcium channels in TC neurons. In the case of high-voltage-activated calcium current, there was no quantitative difference between wild-type and α1G −/− mice, suggesting that the null mutation of α1G does not affect the activities of the high-voltage-activated calcium channels in TC neurons. High-voltage-activated calcium current is a $Ca^{2+}$ current activated by a higher potential than resting membrane potential (−55 mV to −65 mV), and low-voltage-activated calcium current is activated by a lower potential than resting membrane potential.

The present inventors examined whether the loss of T-type calcium currents ($I_T$) affected the intrinsic firing properties of TC neurons. As a result, the α1G −/− mice of the present invention showed a normal pattern of tonic mode firing but showed no burst mode firing. Especially, generation of $GABA_B$ receptor-mediated SWDs in the thalamus, the hallmark of an absence seizure, was suppressed in the α1G −/− mice of the present invention. Therefore, regulation of intrinsic firing pattern mediated by T-type calcium channels containing α1G is closely connected with the genesis of absence seizures. Since the occurrence of generalized seizures (excluding tonic-clonic seizures) and absence seizures were observed in α1G −/− mice, it is suggested that, with a suppression of the function of α1G protein, the occurrence of absence seizures can be avoided. That is, with the function of α1G protein suppressed, episodes of epilepsy exhibiting absence seizure symptoms do not occur.

The present invention also provides a use of an α1G suppressor for the prevention and treatment of epilepsy.

According to the present invention, epilepsy can be prevented or treated by administrating the α1G suppressor to the central nervous system. When there was no function of α1G protein, a structural component of T-type calcium channels, in the central nervous system, absence seizures did not occur. Therefore, the administration of an α1G suppressor results in the standstill of absence seizures, leading to the treatment of epilepsy showing absence seizure symptoms.

Nickel and mibefadil are known suppressors of α1G of T-type calcium channels, and these α1G suppressors can be effectively used for the prevention and treatment of epilepsy.

The present invention also provides a transgenic mouse whose genome comprises a homozygous disruption of its α1G gene, wherein the transgenic mouse does not express α1G protein and is resistant to absence seizure.

Particularly, the present invention provides a homozygote transgenic mouse having α1G −/− genotype that is characterized by the loss of the function of α1G protein.

The present inventors have deposited on Oct. 4, 2001, a sample of embryos of transgenic mice having alpha 1G +/− genotype designated as "TGHS-011 (transgenic mice embryo)" with the Korean Collection for Type Cultures (KCTC) of the Korean Research Institute of Bioscience and Biotechnology (KRIBB) International Depositary Authority, at #52 Oun-dong, Yusong-ku, Taejon 305-333, Republic of Korea, in compliance with the Budapest Treaty on the International Recognition of the Deposit of Microorganisms for the Purpose of Patent Procedure as Deposit Accession Number KCTC 10086BP.

The present inventors hereby assure the United States Patent and Trademark Office and the public that (a) all restrictions on the availability to the public of the deposited material described above will be irrevocably removed upon issuance of a United States patent of which any of such deposited material is the subject;

(b) the deposited material will be maintained for a period of at least five years after the most recent request for the furnishing of a sample of any of the deposited material was received by the KCTC and, in any case, for a period of at least 30 years after the date of deposit or for the effective life of such patent, whichever is longer;

(c) should any of the deposits become non-viable or mutated, or otherwise incapable of being furnished by the depository upon request due to the condition of the deposit, it will be replaced by Applicants; and (d) access to the cultures will be available to the Commissioner during the pendency of the patent application or to one determined by the Commissioner to be entitled to such cultures under 37 C.F.R. §1.14 and 35 U.S.C. §122.

The α1G-knockout mouse having α1G −/− genotype was generated by mating mice obtained from the embryos having α1G +/− genotype.

The α1G-knockout transgenic mouse can be used for investigating the relationship between diseases particularly neuropathy or psychopathy and the function of α1G T-type calcium channel via various behavioral tests since α1G subunit is mainly expression in central nervous system (CNS) and pheripheral nervous system (PNS). The behavioral tests are well known in the art. Giorgio Bignami teaches various behavioral tests such as a suckling test and a homing test (Bignami, G., *Environ. Health Perspect.*, 104(S2): 285-298, 1996). Further, Nomura et al. teaches a forced swimming test for screening antidepressants (Nomura, S. et al., *Eur. J. Pharmacol.*, 83(3-4): 171-175, 1985). Steru et al. teaches a tail suspension test for screening antidepressants (Setru, L. et al., Psychopharmacology (Berl), 85(3): 367-370, 1985). Rostock et al. teaches an active avoidance test for screening memory enhancing drugs (Rostock, A. et al., *Methods Find Exp. Clin. Pharmacol.*, 1(9): 547-553, 1989). Labuda et al. teaches to a behavioral test for assessing nociception in rat neuropathic and inflammatory models (Labuda, C. J. et al., *Exp. Neurol.* 163(2): 490-494, 2000). McIlwain et al. teaches a behavioral test battery for the initial assessment of phenotypic behavioral differences of transgenic, knockout, and inbred strains of mice (McIlwain, K. L. et al., *Physiol. Behav.* 73(5): 705-717, 2001). For example, one can perform the forced swimming test or the tail suspension test using the α1G knock-out transgenic mice of the present invention and normal mice (control) in order to investigate whether α1G T-type calcium channel is related in depression. If the α1G knock-out transgenic mice show severer symptom of depression rather than control, one can use the α1G knock-out transgenic mice as model animals for depression. On the contrary, if the α1G knock-out transgenic mice show alleviated symptom of depression rather than control, one can investigate whether the T-type calcium channel blocker can alleviate depression.

In deed, the present inventors performed a behavioral test with respect to absence seizure using the α1G knock-out transgenic mice whether the α1G T-type calcium channel is related to absence seizure and found that the α1G knock-out transgenic mice show resistance against absence seizure as described above.

In addition, the present invention provides a method for screening an agent for treating absense seizure using the transgenic mouse comprising:

(a) administrating an absence seizure-inducing agent to a group of wild type mice and a group of the transgenic mice;

(b) administrating drug candidates to the group of the wild type mice and the group of transgenic mice of step b;

(c) comparing electophysiolgical or behavioral traits with respect to absence seizure of the group of wild type mice and the group of the transgenic mice of step c; and (d) selecting a drug candidate which alleviates the electrophysiological or behavioral traits of the group of wild type mice on a level with those of the transgenic mice.

In an embodiment, the absence seizure-inducing agent is (RS)-baclofen or γ-butyrolactone but not limited thereto.

In another embodiment, the electrophysiological trait is a burst-mode firing, spike-and-wave discharges (SWDs), intrathalamic SWDs but not limited thereto.

In a sill another embodiment, the behavioral trait is selected from the group consisting of:
  i) mild tremors of the head;
  ii) whole body tremors with loss of postural control;
  iii) erratic running, erratic jumping, or tonic-clonic movement of the limbs; and
  iv) tonic extension of the whole body or death.

The method of present invention may further comprises administrating 4-AP as a convulsive seizure-inducing agent in said step (a) in order to the drug candidate is specific for absence seizure rather than convulsive seizure.

The transgenic mouse of the present invention can be used for screening antileptic agents. Particularly, the transgenic mouse of the present invention can be a standard for identifying whether a compound or a composition have antileptic activity by comparing behavioral properties regarding seizure of wild type mice and the transgenic mice whereto the compound or the composition and an epilepsy-inducing agent are administrated. If the wild type mice show alleviated symptom of epilepsy as the transgenic mice do, one can conclude that the compound or the composition be used for antileptic agents.

The present invention also provides a preparation method of an α1G-knockout mouse having α1G −/− genotype.

The preparation method of a homozygote transgenic mouse having α1G −/− genotype comprises four steps:

(1) inserting a targeting vector of α1G gene of T-type calcium channels into mouse embryonic stem cells;

(2) obtaining a chimera mouse by injecting the mouse embryonic stem cells into blastocoel;

(3) obtaining α1G +/− heterozygote mouse by mating the chimera mouse and a wild-type mouse; and (4) obtaining α1G −/− homozygote by mating a female α1G +/− heterozygote mouse and a male α1G +/− heterozygote mouse.

Using a gene targeting method, the present inventors constructed a targeting vector containing a gene coding, N'-deleted α1G of T-type calcium channels. The targeting vector of the present invention includes a homologous fragment of gene coding N'-deleted α1G protein, PGK-neo cassette, and thymidine kinase gene cassette located at 3'-end. Since homologous recombination takes place at the homologous fragment and N'-end of α1G protein is deleted, wild-type α1G gene of the calcium channel is not expressed by the above targeting vector.

In the preferred embodiments of the present invention, the present inventors generated a chimera mouse by inserting the cultured embryonic stem cell clone having targeted α1G gene into blastocoel of the blastula. After mating a female mouse having embryonic stem cell-inserted blastula with a male mouse having undergone vasectomy, transplantation was performed into a uterus of a 2.5 p.c. surrogate mother mouse. The surrogate mother mouse was raised for nineteen days, from which chimera mice having α1G +/− genotype were obtained. Finally, the present inventors generated a homozygote F2 transgenic mouse having α1G −/− genotype by mating a male and a female mouse selected from the above F1 mice having α1G +/− genotype.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Generation of Targeting Vector and Transfection

<1-1> Generation of Targeting Vector

To generate a knockout mouse for the α1G subunit of T-type calcium channel, the present inventors carried out a gene targeting method.

Particularly, a mouse cDNA of the α1G gene (cacna1G) sequence corresponding to 688-1008 bp of the rat cDNA was isolated by RT-PCR. Using the above isolated sequence as a probe, a bacteriophage lambda FIX II library (Stratagene) wherein DNA fragments of 129/sv mouse genome were inserted randomly was screened. From this, the genomic phage clone containing α1G gene was selected and confirmed by restriction mapping, Southern blotting, and sequencing.

Figure 1A:
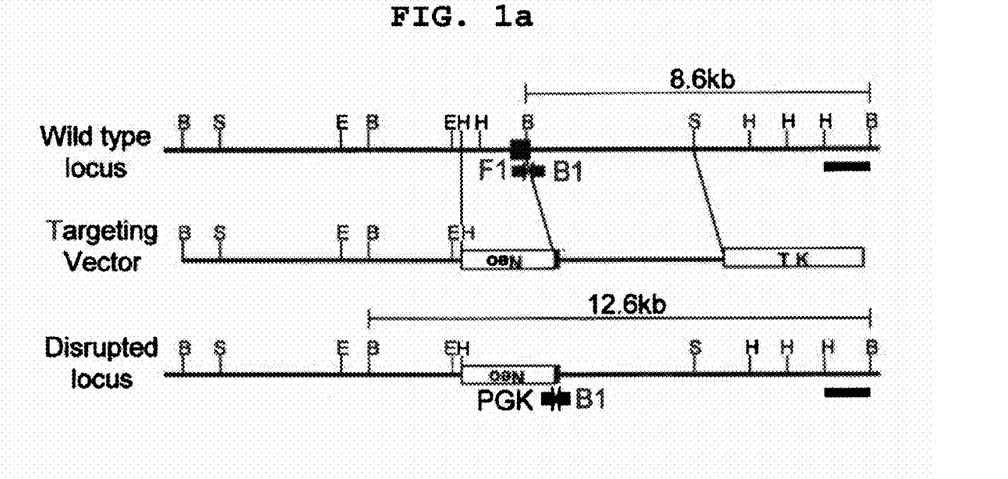
FIG. 1A is a schematic diagram showing the structure of a wild-type α1G locus, a targeting vector, and a disrupted α1G locus.

The targeting vector was designed to delete most of the exon encoding amino acid residues 82-118 that comprise the N-terminus of the α1G protein. To enhance targeting efficiency, a thymidine kinase gene cassette and a negative selection marker were inserted into the 3' of the targeting vector (FIG. 1A).

<1-2> Culture of Embryonic Stem Cell

A J1 embryonic stem cell line was used for the transfection of the targeting vector generated in Example <1-1>. J1 embryonic stem cells (obtained from Dr. R. Jeanisch of the Massachusetts Institute of Technology) were maintained in DMEM (Gibco Co.) supplemented with 15% fetal bovine serum (Hyclone Co.), 1× penicillin-streptomycin (Gibco Co.), and 1× non-essential amino acid (Gibco Co.) for two to three days at 37° C. Single cells were obtained by treating the cells with 1 mM EDTA solution containing 0.25% trypsin.

<1-3> Transfection of Targeting Vector

The targeting vector generated in Example <1-1> was transfected by electroporation into the single cells obtained in Example <1-2>. Particularly, 25 μg of targeting vector DNA was added into embryonic stem (ES) cells (2×10⁷ cells/Ml). After mixing, electroporation was performed with 270 V/500 μF. The cells were cultured in an ES medium containing 0.3 mg/Ml of G418 and 2 μM of gansiclover for five to seven days. ES cell clones correctly targeted were selected by using homologous recombination method, and maintained.

<1-4> Southern Blot Analysis

To find ES clones correctly targeted from the clones selected in Example <1-3>, genomic DNA was extracted from each clone and Southern blot analysis was performed. Particularly, genomic DNA extracted from each clone was digested with restriction enzyme BamH I, and hybridization was performed by using bar (−) region of FIG. 1A as a DNA probe.

Figure 1B:
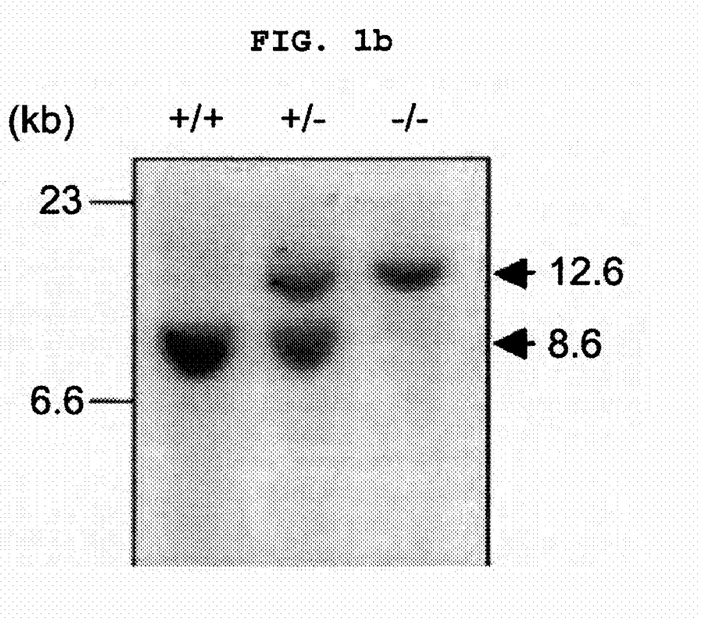
FIG. 1B is an electrophoresis photograph showing the results of Southern blot analysis of α1G −/− mice of the present invention.

As a result, only the 8.6 kb band was observed in normal cells, in which a targeting vector was not introduced, whereas 8.6 kb and 12.6 kb bands were observed in α1G-deficient clones (FIG. 1B). Therefore, it was confirmed that the clones were deficient of the calcium channel α1G gene by introducing a targeting vector and have an α1G +/− genotype. Alpha 1G-deficient ES clones were cultured in an ES medium for 18-22 hours, and single cells were obtained by treating the clones with trypsin. Surviving cells were selected and used for microinjection.

Example 2

Generation of Chimera Mice

To generate chimera mice having α1G +/− genotype, embryonic stem cell clone selected in Example <1-3> was microinjected into fertilized blastula. Particularly, female and male C57BL/6J mice (obtained from the Jackson Laboratory of Bar Harbor, Me.) were mated, and three and a half days after mating, the female mouse was sacrificed by cervical dislocation. Uterus was removed from the sacrificed female mouse and the terminal region of the uterus was cut with scissors. Using a 1 Ml syringe, 1 Ml of injection solution containing 20 mM HEPES, 10% FBS, 0.1 mM 2-mercaptoethanol, and DMEM was circulated. Blastula was separated from the uterus using microglasstube under the dissecting microscopy. The separated blastula was transferred to a drop of injection solution and placed on a 35 mm petri dish. Ten to fifteen embryonic stem cell clones were inserted into blastocoel of the blastula by using a micro-injector (manufactured by Zeiss of Germany). The above blastula was transplanted into a uterus of a surrogate mother mouse to develop a chimera mouse. The surrogate mother mouse was raised for nineteen days, from which chimera mice having α1G +/− genotype were obtained.

Example 3

Generation of α1G +/− Heterozygote Mice

Among offspring generated from mating a C57BL/6J female mouse with a male chimera mouse obtained in Example 2, genetically stable heterozygote F1 transgenic mice were selected. PCR was performed to select heterozygote mice having α1G +/− genotype among them. DNA for PCR was extracted from the tails of the mice. Particularly, 1.5 cm of mice tail was cut and dipped in 0.4 ml of lysis buffer containing 100 mM Tris-HCl (pH 8.0), 5 mM EDTA, 200 mM NaCl, and 0.2% SDS. Proteinase K (0.1 mg/ml) was added to the above solution and reacted at 55° C. for five hours. Thereafter, 75 μl of 8 M potassium acetate and 0.4 ml chloroform was added and the resultant was agitated. The solution was suspended at 4° C. for ten minutes. Supernatant and sediment were separated by centrifugation at 15,000 rpm. One milliliter of ethanol was added to the 0.4 ml of separated supernatant to precipitate genomic DNA. The precipitated genomic DNA was washed with 70% ethanol. After drying, the genomic DNA was resolved in 50 μl of distilled water and used for PCR.

One microliter of the above DNA was used as a template for PCR reaction. SEQ. ID. NO:1 (F1), NO:2 (B1), and NO:3 (PGK22) were also used as primers for the PCR. The F1-B1 primer set was designed to amplify a 288 bp DNA fragment of wild-type α1G gene, and the PGK22-B1 primer set was designed to amplify a 385 bp DNA fragment of transgenic gene. For the control, DNA extracted from wild-type mice was used.

Figure 1C:
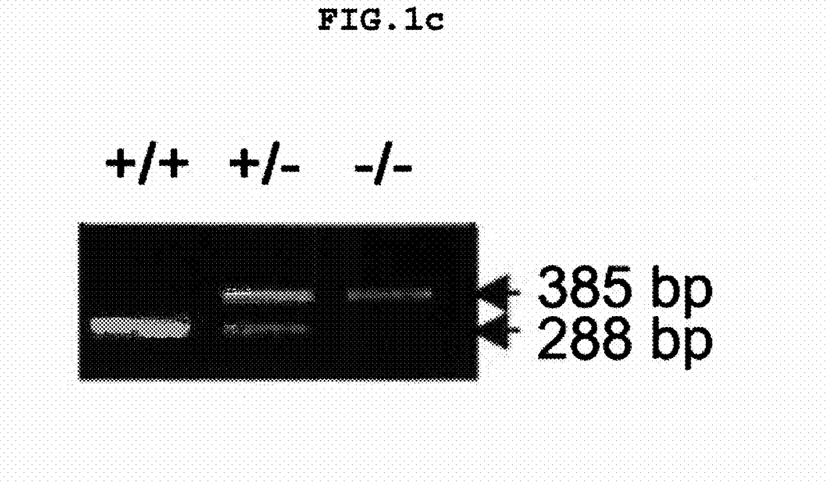
FIG. 1C is an electrophoresis photograph showing the results of a polymerase chain reaction (PCR) of α1G −/− mice of the present invention.
Figure 1D:
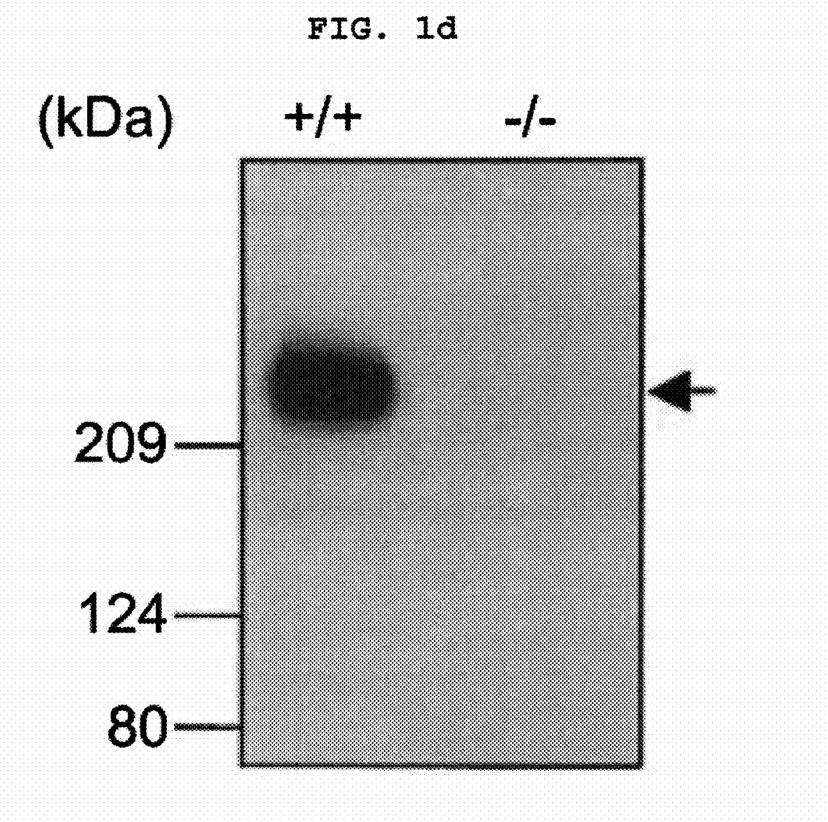
FIG. 1D is an electrophoresis photograph showing the results of Western blot analysis confirming that T-type calcium (Ca$^{2+}$) channel α1G protein was not expressed in the brain of α1G-knockout mice of the present invention.

As a result, heterozygote mice having α1G +/− genotype was confirmed by observing that the mice showed two different bands; one is a targeting α1G gene-amplified 385 bp band and the other is a wild-type α1G gene-amplified 288 bp band (FIG. 1C).

Example 4

Generation of Homozygote Transgenic Mice Having α1G −/− Genotype

Homozygote transgenic mice having α1G −/− genotype were generated by mating a male and a female heterozygote mouse having α1G +/− genotype, which were selected in Example 3. Southern blot analysis and PCR were performed to confirm whether the above homozygote transgenic mice had α1G −/− genotype. Western blot analysis was also performed to confirm that α1G protein was not expressed in the transgenic mice.

<4-1> Southern Blot Analysis

Genomic DNA was extracted from transgenic mouse tail with the same method as Example 3 and digested with BamH I. Hybridization was performed using DNA probe obtained from phage DNA of Example <1-4> and the above mouse DNA. Genomic DNA extracted from wild-type and transgenic mouse having α1G +/− genotype were used as controls.

As shown in FIG. 1B, an 8.6 kb band originating from a normal α1G gene was detected in wild-type mouse (Lane 1), and along with the 8.6 kb band, a 12.6 kb band was also detected in heterozygote mouse (Lane 2). Meanwhile, only the 12.6 kb band originating from the α1G −/− gene was detected in homozygote mouse (Lane 3), confirming that homozygote transgenic mice of the present invention have α1G −/− genotype.

<4-2> Polymerase Chain Reaction

After extracting genomic DNA from transgenic mouse tail with the same method as Example 3, PCR was performed under the conditions of Example 3. That is, 1 μl of genomic DNA was used as a template and the same primers of Example 3 were used.

As shown in FIG. 1C, a 288 bp PCR product amplified from normal α1G gene was detected in wild-type mouse (Lane 1), along with the 288 bp band, a 385 bp PCR product amplified from the α1G +/− gene was detected in heterozygote mouse (Lane 2). Meanwhile, only the 385 bp PCR product was detected in homozygote mouse (Lane 3), suggesting that the homozygote transgenic mice of the present invention has α1G −/− genotype, which is the same result as that of the above Southern blot analysis.

<4-3> Antibody Production and Western Blot Analysis

The present inventors performed Western blot analysis to confirm that α1G gene was not expressed in α1G −/− mice of the present invention.

Anti-α1G antibodies were raised to the following epitope (represented by the SEQ. ID. NO:4) that was conjugated to keyhole limpet hemocyanin and injected into rabbits. Serum (CW53) was affinity purified over Sulfolink columns that had the antigenic peptide immobilized via the cysteine linkage. The columns were washed with TBS, and the antibodies eluted with increasing concentrations of glycine and dialyzed overnight. Following anesthesia, the whole brains were isolated from the mice and were homogenized in a cold lysis buffer of 50 mM Tris/HCl (pH 7.4), 1 mM EGTA, 1 mM DTT, 1 mM PMSF, a Complete protease inhibitor cocktail (manufactured by Boehringer Mannheim), and Calpain inhibitors I and II. After low-speed centrifugation (1000 g, five minutes), supernatants were centrifuged (28,000 g, fifteen minutes) to obtain crude membrane fractions. The crude membrane fractions were separated in gradient SDS PAGE gels (8%-16%), blotted to nitrocellulose membranes (Protran manufactured by Schleicher & Schuell), and visualized by the anti-α1G affinity-purified polyclonal antibodies by enhanced chemiluminescence.

As a result, α1G protein was not detected in the α1G −/− brain, whereas the protein was detected in the wild-type (+/+) mouse brain. Therefore, it was confirmed that α1G of T-type calcium channel protein was not expressed in knockout mice of the present invention by lacking the α1G gene (FIG. 1C).

<4-4> Assay of Functional Loss of a 1G

Figure 2A:
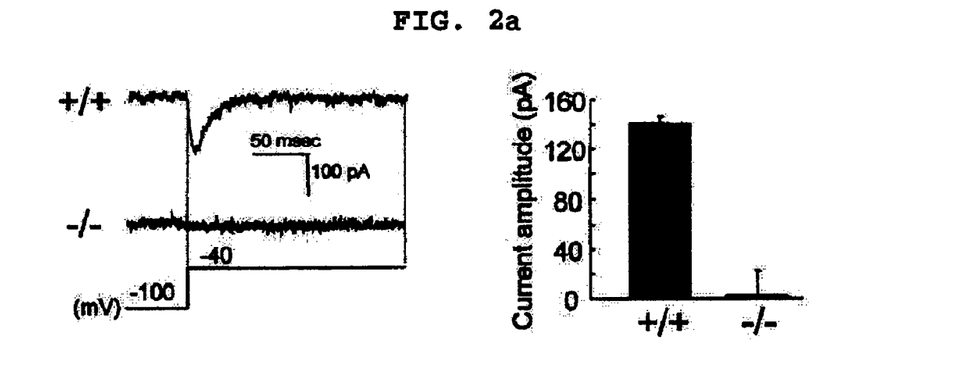
FIG. 2A is graphs showing the results of whole-cell voltage clamp analysis of low-voltage-activated (LVA) T-type calcium current in wild-type and in α1G-knockout mice of the present invention.

The functional loss of α1G was examined by whole-cell voltage-clamp analysis of low-voltage-activated T-type calcium current in TC neurons acutely isolated from α1G −/− and wild-type (+/+) mice. Step voltage changes from holding potentials of −100 mV to −40 mV evoked low-voltage-activated calcium current that were completely inactivated within 50 milliseconds (ms) in wild-type thalamocortical cells. In contrast, calcium current: was completely absent in the α1G −/− TC neurons, suggesting that α1G is the major component of the T-type calcium channels in TC neurons (FIG. 2A).

Figure 2B:
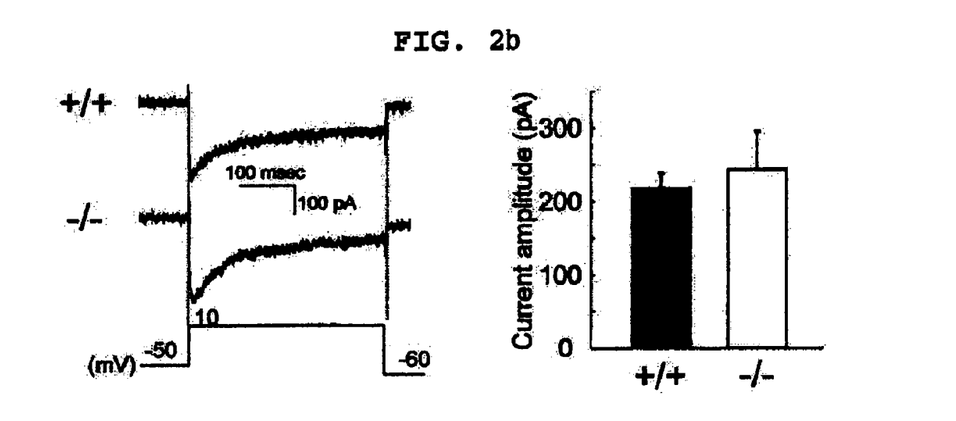
FIG. 2B is graphs showing the results of whole-cell voltage clamp analysis of high-voltage-activated (HVA) T-type calcium current in wild-type and in α1G-knockout mice of the present invention.

The present inventors also examined high-voltage-activated calcium current using a depolarizing voltage step from −50 mV to 10 mV (FIG. 2B). Both wild-type (n=5) and α1G −/− (n=5) TC neurons produced a slowly inactivated high-voltage-activated calcium current, with no significant quantitative difference between the two groups in the peak amplitude of the high-voltage-activated calcium current. These results suggest that the null mutation of α1G did not affect the activities of the high-voltage-activated calcium channels in TC neurons.

In addition, general development of the brain of the α1G −/− mice appeared normal, as judged by an analysis of Nissle-stained serial sections. All major cytoarchitectonic divisions in the thalamus, cortex, and cerebellum, which express the α1G gene, were unchanged. There were no significant histological defects in organs obtained from the α1G −/− mice, including the heart, pancreas, intestine, liver, and kidney.

Example 5

Burst and Tonic Firing Patterns of α1G −/− Mice

The present inventors examined whether the loss of T-type calcium current affected the intrinsic firing properties of TC neurons located within the ventrobasal complex.

Using a vibratome, 350 μm-thick slices of coronal, corresponding to regions containing ventrobasal complex (usually between −1.2 mm and −2.5 mm from the bregma), were prepared in oxygenated, cold, artificial cerebrospinal fluid (ACSF, 126 mM NaCl, 2.5 mM KCl, 1.25 mM $MaH_2PO_4$, 2 mM $CaCl_2$, 2 mM $MgSO_4$, 26 mM $NaHCO_3$, and 10 mM dextrose, pH7.4). Slices were then placed at an interface of air and artificial cerebrospinal fluid in a warm, humidified (30° C., 95% $O_2$ and 5% $CO_2$) recording chamber. Intracellular recording electrode (borosilicate glass, 40-80MΩ) were filled with 3M potassium acetate and positioned in the ventrobasal complex. The ventrobasal complex was identified under a dissecting microscope (manufactured by World Precision) using the medial leminiscus and internal capsule as landmarks. Signals were amplified by a high-impedance amplifier that used an active bridge to allow capacitance compensation and by current injection through a recording electrode (AxoClamp-2B manufactured by Axon Instruments). Data analysis software included pCLAMP, Axoscope (manufactured by Axon Instruments), and SigmaPlot (developed by SPSS Science).

As a result, resting membrane properties of the thalamocortical cells were not significantly different between the wild-type (n=35) and α1G −/− (n=33). That is, the resting membrane potential was 61±4.7 mV in wild-type and 59±3.7 mV in α1G −/− (Student's t-test, P>0.05), and the input resistance was 87.7±15 MΩ in wild type and 93.1±8 MΩ in α1G −/− (Student's t-test, P>0.05).

Figure 3A:
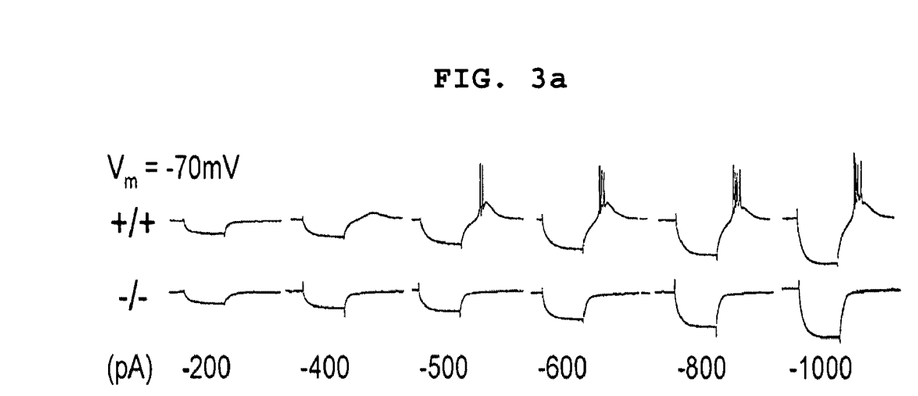
FIG. 3A is a graph showing the burst firing patterns elicited by negative current in wild-type and in α1G-knockout mice of the present invention.

When a negative current input was delivered at a holding membrane potential of −70 mV, a rebound LTCP was triggered with a burst of action potentials at a frequency of 200-500 Hz in wild-type thalamocortical cells (94% of 47/50 cells examined, FIG. 3A). The burst-mode firing was also elicited by a positive current input at a holding membrane potential of −80 mV in wild-type TC neurons (Huguenard and Prince, *Journal of Neurophysiology*, 1994, 71, 2576-81). In contrast, such burst firing of action potentials was not observed in the α1G −/− TC neurons (0% of 0/36 cells examined).

Figure 3B:
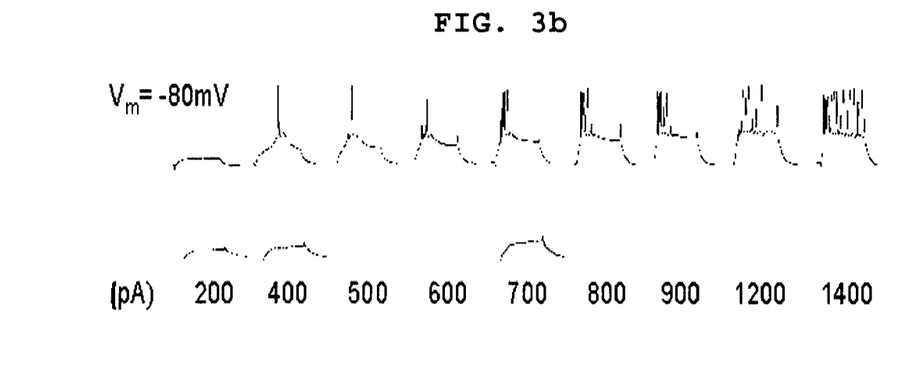
FIG. 3B is a graph showing the burst firing patterns elicited by positive current in wild-type and in α1G-knockout mice of the present invention.
Figure 3C:
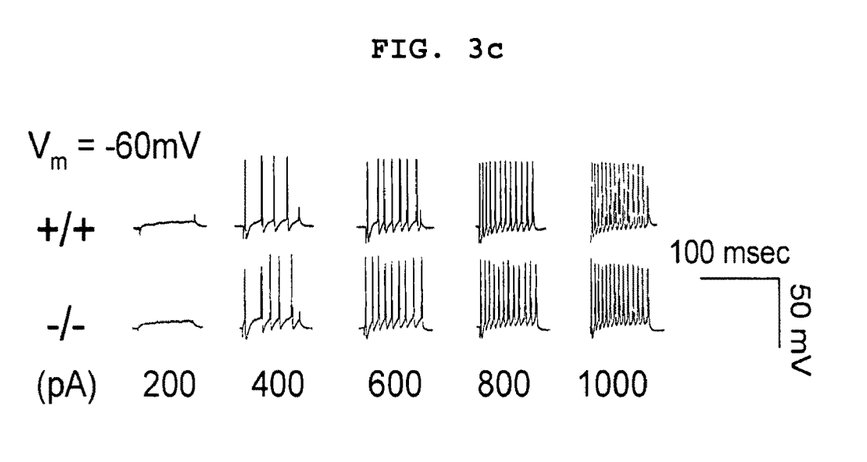
FIG. 3C is a graph showing the tonic firing patterns elicited by positive current in wild-type and in α1G-knockout mice of the present invention.

However, increasing the amount of depolarizing currents input in the α1G −/− TC neurons eventually evoked a number of action potentials (FIG. 3B), the frequency of which appeared to be that of a tonic firing of action potentials (100-200 Hz). To test this, the present inventors compared wild-type and α1G −/− thalamocortical cells with respect to the tonic-firing pattern triggered by depolarizing positive current inputs at −60 mV, but no significant difference was noted between the two groups in the pattern or the number of spikes generated (FIG. 3C).

Figure 3D:
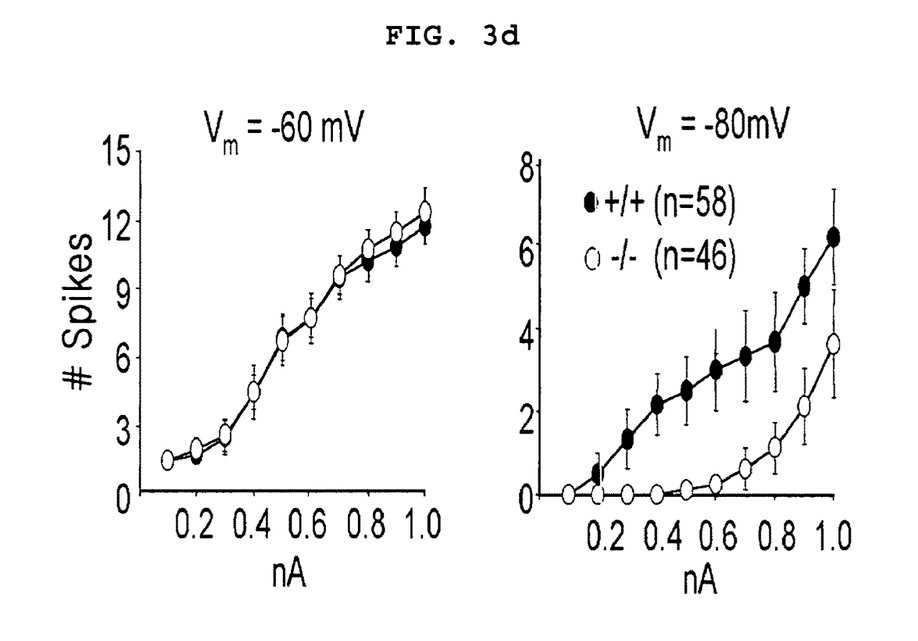
FIG. 3D is graphs showing the relation between the number of spikes and the amount of current injected.

There was a quantitative difference between wild-type and α1G −/− TC neurons in the number of spikes in the burst mode, however, no such difference between the two genotypes was observed in tonic-mode firings (FIG. 3D). This suggested that the α1G null mutation selectively affects the burst-mode firing in the α1G −/− TC neurons.

Example 6

Analysis of SWD Generation in α1G −/− Mice

Figure 4A:
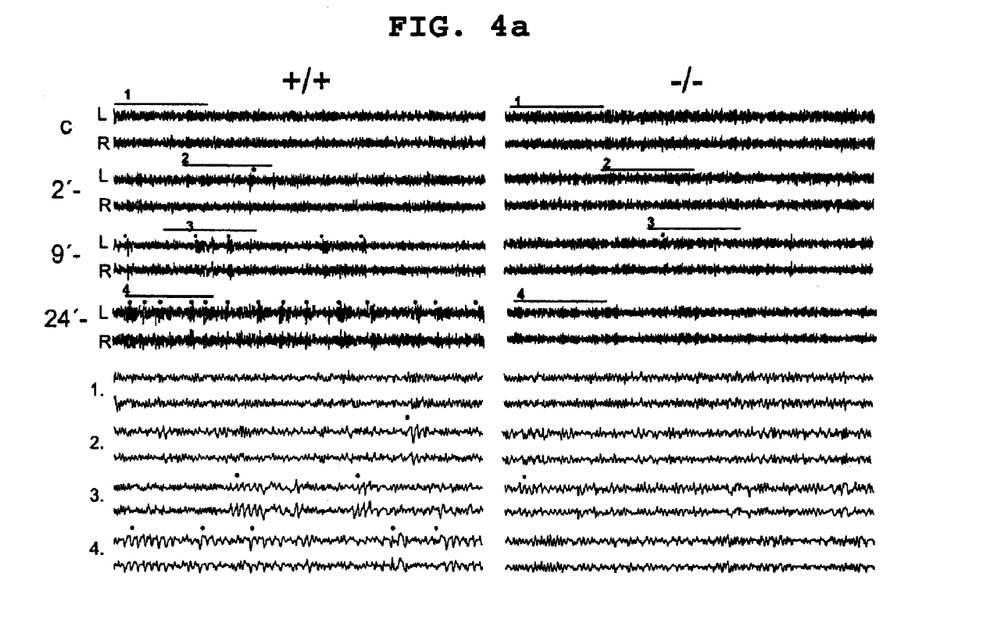
FIG. 4A is graphs showing the EEG patterns of wild-type and of α1G-knockout mice of the present invention, after treatment with γ-butyrolactone.
Figure 4B:
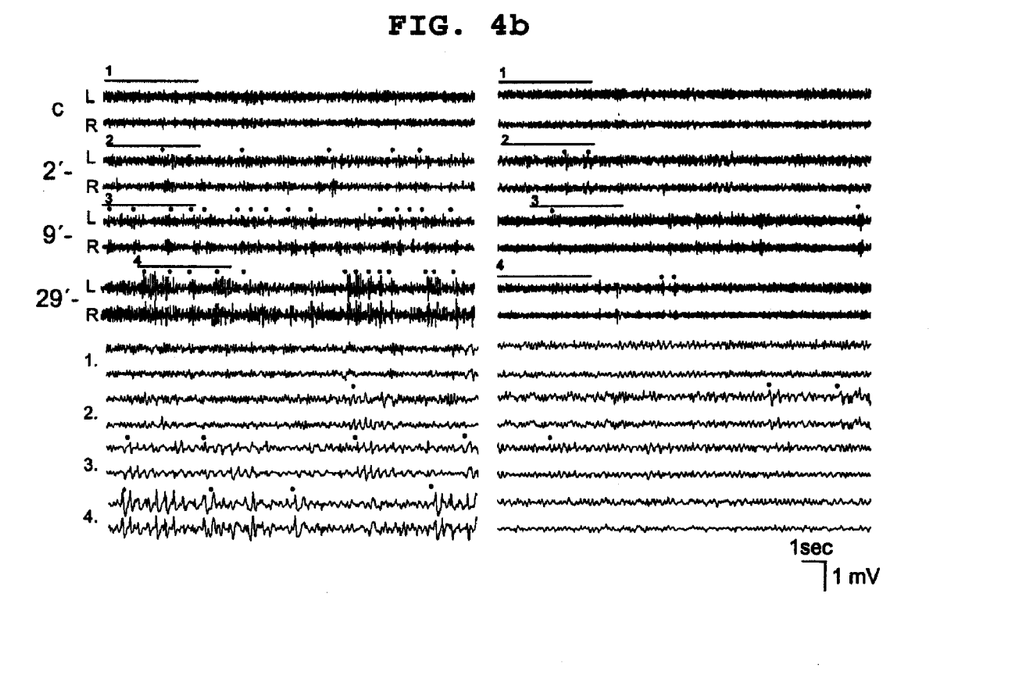
FIG. 4B is graphs showing the EEG patterns of wild-type and of α1G-knockout mice of the present invention, after treatment with (RS)-baclofen.
Figure 4C:
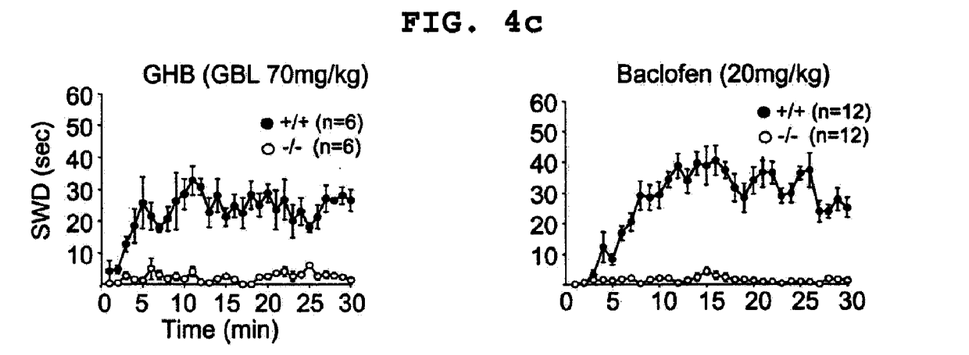
FIG. 4C is graphs showing the quantitative differences of SWDs induced either by γ-butyrolactone or (RS)-baclofen.

To examine the role of α1G in the generation of SWDs in vivo, the present inventors systematically ["systemic" and "systematic" are different] injected into α1G −/− mice and wild-type mice either γ-butyrolactone, a prodrug of γ-hydroxybutyric acid, or (RS)-baclofen. Absence seizures induced by these drugs are characterized by bilaterally synchronous SWDs and have been associated with behavioral arrest, facial myoclonus, and vibrissal twitching. When administered with γ-butyrolactone at 70 mg/kg, the epidural EEG of wild-type mice (n=8) showed 3-5 Hz paroxysmal SWDs (FIG. 4A). In contrast, α1G −/− mice (n=8) did not display typical SWD patterns after administration of γ-butyrolactone, although 3-4 Hz bilaterally synchronous oscillations of shorter duration were sporadically observed (FIG. 4A). Similarly, while wild-type mice showed 3-4 Hz SWDs in response to (RS)-baclofen injection at 20 mg/kg, α1G −/− mice showed a marked resistance to the generation of SWDs in response to (RS)-baclofen injection at 20 mg/kg (FIG. 4B). A quantitative difference in the genesis of absence seizures between wild-type and α1G −/− mice during thirty minutes after the administration of either drug was showed in FIG. 4C (ANOVA, $p<0.001$).

Therefore, it was confirmed that the absence seizures did not occur in the α1G −/− mice of the present invention, even after treating with (RS)-baclofen or γ-butyrolactone, which are known absence seizure-inducing agents.

Example 7

Figure 5A:
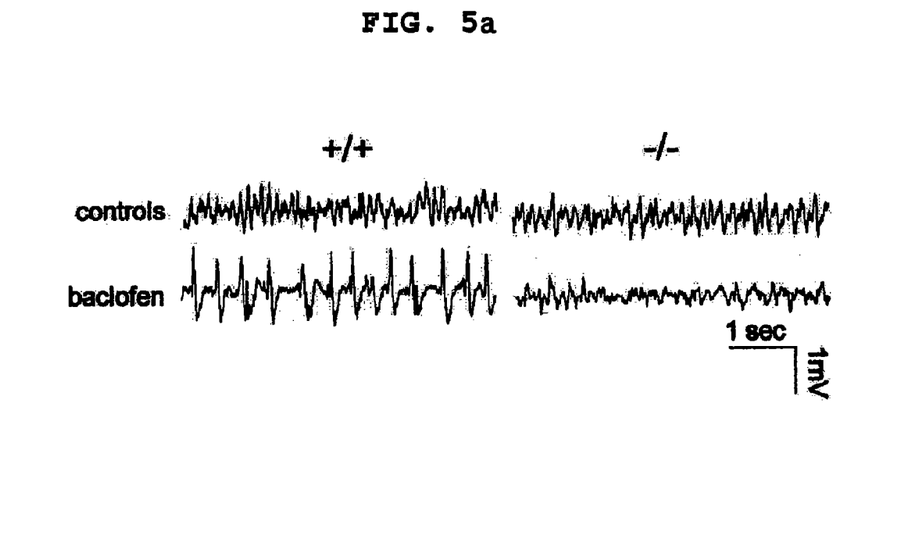
FIG. 5A is graphs showing the field recording of wild-type and of α1G-knockout mice of the present invention, after treatment with (RS)-baclofen.
Figure 5B:
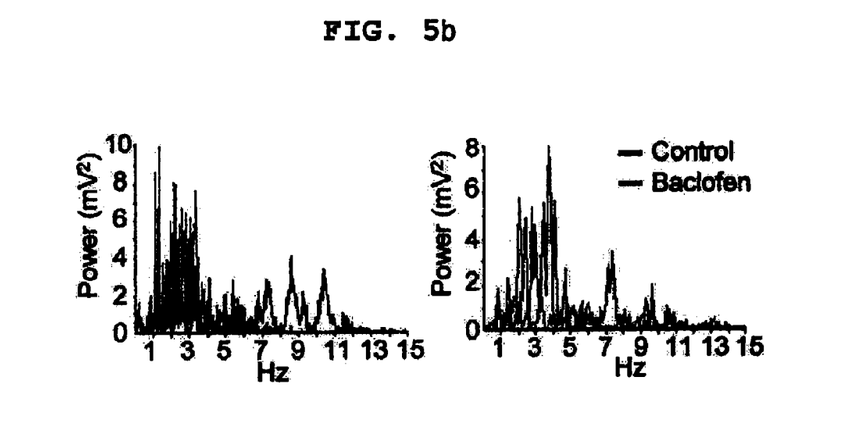
FIG. 5B is graphs showing the results of power spectral analysis of the field potentials before and after (RS)-baclofen treatment.

Analysis of Intra-Thalamic Oscillation in Response to Baclofen-Mediated Hyperpolarization in α1G −/− Mice To confirm the result of Example 6, the present inventors examined the field activity of thalamic nuclei using depth electrodes in freely moving animals. In visual inspections, the field activities of the wild-type and α1G −/− mice were not significantly different (FIG. 5A), except for activity with frequency at 10-12 Hz, which was weaker in the α1G −/− thalamus than in the wild-type thalamus (FIG. 5B). To examine the thalamic SWDs, the present inventors injected (RS)-baclofen i.p. at 30 mg/kg instead of the dose, i.e., 20 mg/kg, used previously (FIG. 4B). While 20 mg/kg baclofen generated 3-4 Hz paroxysmal SWDs (FIG. 4B), the higher dose of baclofen, i.e., 30 mg/kg, significantly increased the duration of SWDs with a slight reduction in frequency (2-3 Hz) in epidural EEG. In the wild-type thalamus, prominent 2-3 Hz SWDs were evoked by 30 mg/kg of baclofen, but no such synchronized activities were observed in the α1G −/− thalamus (FIG. 5A). The administration of baclofen synchronized all thalamic activities into 2-3 Hz SWDs in wild-type nice (FIG. 5B, left). In the α1G −/− thalamus, however, baclofen reduced the amplitudes of peaks in a wide range of frequency, as if it caused general desynchronization (FIG. 5B, right). From the above results, it was confirmed that the absence seizures generated by baclofen did not occur in the α1G −/− mice of the present invention.

Example 8

Analysis of SWDs Generation in α1G −/− Mice After Administration of a $GABA_A$ Antagonist Systematic administration or focal injection of bicuculline into the cortex has been known to evoke SWDs mainly originating from the territory of the cortex (Steriade and Contreras, *Journal of Neurophysiology*, 1998, 80, 1439-55). To determine the role of α1G in the cortex-dependent mechanism of SWDs, the present inventors examined the EEG pattern after injection of BMB into the peritoneal cavity of mice at 10 mg/kg.

Figure 6A:
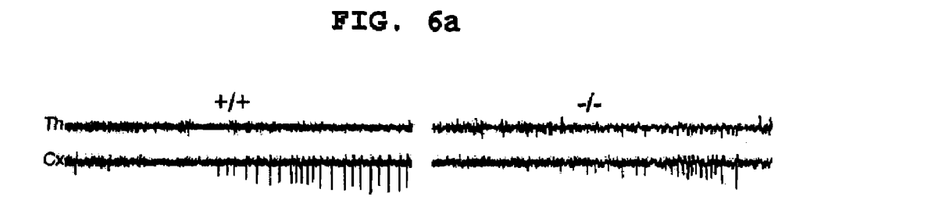
FIG. 6A is graphs showing an EEG recording of the thalamus and cortex, taken after administration of BMB in wild-type and in α1G-knockout mice of the present invention.
Figure 6B:
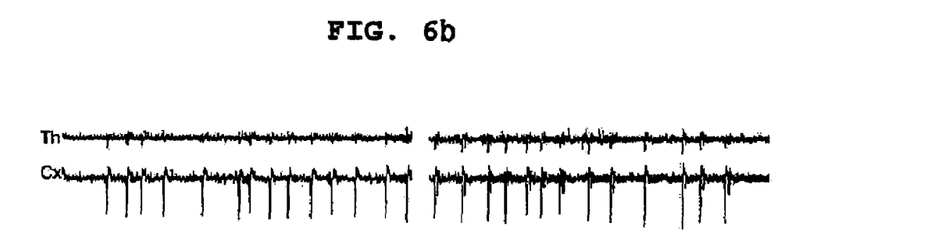
FIG. 6B is graphs showing an EEG recording of the thalamus and cortex, taken ten minutes after an administration of BMB.
Figure 6C:
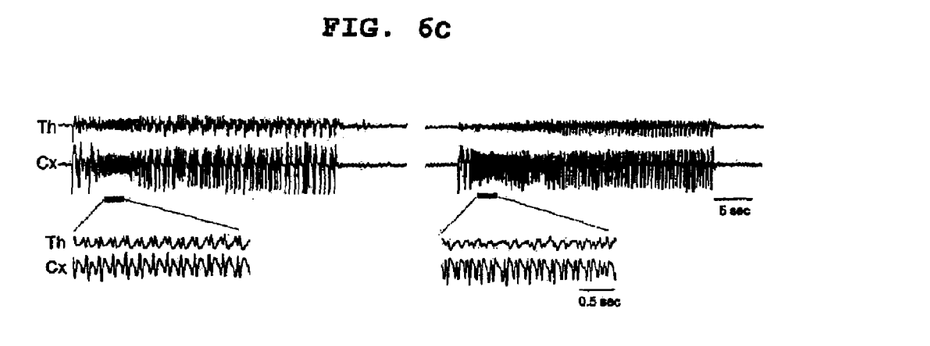
FIG. 6C is graphs showing the patterns of SWDs observed during BMB-induced seizures, where "Th" denotes thalamus and "Cx" denotes cortex.

As a result, simultaneous EEG recording of the cortex and thalamus showed that seizure spikes were initiated in the cortex within five minutes of the administration of BMB (FIG. 6A), then increased in amplitude (FIG. 6B), and eventually developed highly synchronous SWDs in both the thalamus and cortex (FIG. 6C). In contrast to the case of baclofen injection, α1G −/− mice also exhibited SWD-like activities in response to BMB. However, because of the complexity of the bicuculline-induced seizures, the present inventors could not conclude whether there is any quantitative difference in the amplitude of the SWDs or in the time lag of SWD occurrences for the two types of mice (i.e., wild-type and α1G −/−). At the administrated dose of BMB, mice initially showed immobility with vibrissal twitching, but eventually developed complex types of behavioral seizures such as sudden jumping, loss of postural control, or vocalization. Thus, it seems that the BMB-induced SWDs observed here are also associated with other types of generalized seizures.

Example 9

Analysis of Seizure Resistance of α1G −/− Mice

Figure 7A:
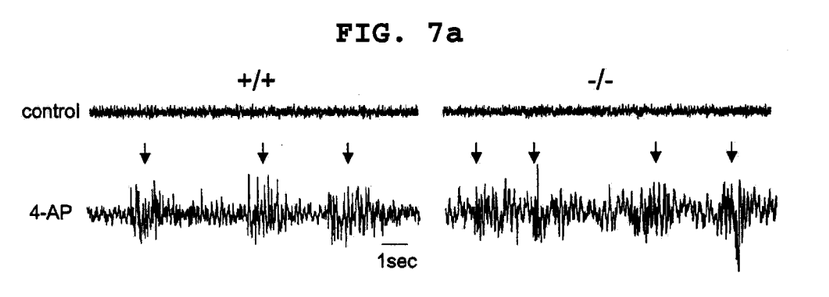
FIG. 7A is graphs showing ictal discharges occurring one hour after an administration of 10 mg/kg 4-AP, where "↓" denotes an instance of ictal discharge when a behavioral seizure has occurred.

The present inventors tested whether the seizure resistance of α1G −/− mice was specific to absence seizures. To achieve this, convulsive seizures were induced by injecting 4-AP, an antagonist for potassium channels, into the peritoneal cavity. 4-AP causes membrane excitability by depolarizing the membrane potential, thereby causing epoleptiform discharges characterized by limbic seizures at the behavioral level (Avoli, *Epilepsia*, 1996, 37, 1035-42). All of the mice treated with 4-AP at 10 mg/kg developed tonic-clonic seizures (C57BL/6J, n=10; 129/sv, n=10), and 25% of mice developed seizures at 2 mg/kg (C57BL/6J, n=10; 129/sv, n=10). Both wild-type and α1G −/− mice developed vigorous ictal discharges 30-40 minutes after injection with 4-AP at 10 mg/kg (FIG. 7A). The EEG pattern of these ictal discharges was quite different from that observed in the spike-and-wave seizures induced by baclofen or bicuculline. The severity of the 4-AP-induced seizures, graded by behavioral symptoms, showed no quantitative difference between wild-type: and α1G −/− mice (FIG. 7A, Student's t-test, $p>0.05$). Both groups showed a similar susceptibility even when a low dose of 4-AP (2 mg/kg) was administered.

Figure 7B:
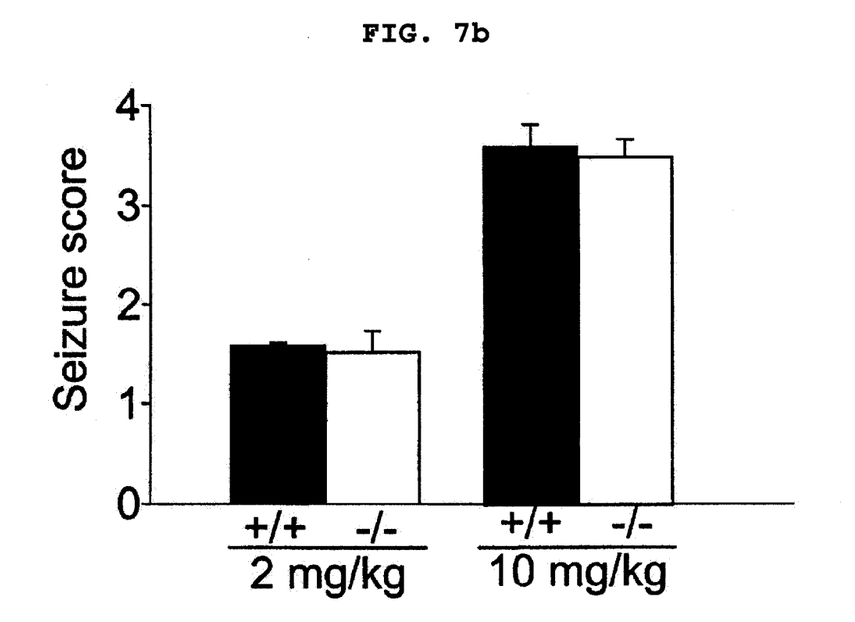
FIG. 7B is a graph showing seizure scores of generalized seizures induced by 4-AP at 2 mg/kg and at 10 mg/kg.

Seizure scores of generalized seizures induce d by 4-AP at 2 mg/kg and at 10 mg/kg are shown in FIG. 7B. The below scores grade the seizures according to behavioral seizures as monitored by video.

0: no behavioral changes
1: mild tremors of the head
2: whole body tremors with loss of postural control
3: erratic running, erratic jumping, or tonic-clonic movement of the limbs
4: tonic extension of the whole body or death The severity of the 4-AP-induced seizures showed no quantitative difference between wild-type and α1G −/− mice.

INDUSTRIAL APPLICABILITY

As shown above, a method of the present invention, whereby the function of α1G protein in T-type calcium channels is suppressed, can be effectively used for the prevention and treatment of epilepsy. The α1G-knockout transgenic mouse can be used for investigating the relationship between diseases particularly neuropathy or psychopathy and the function of α1G T-type calcium channel via various behavioral tests since α1G subunit is mainly expression in central nervous system (CNS) and pheripheral nervous system (PNS). Further, the α1G-knockout transgenic mouse can be used for screening antileptic agents.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A transgenic mouse whose genome comprises a homozygous disruption of its α1G gene, wherein the transgenic mouse does not express α1G protein and is resistant to absence seizure.

2. The transgenic mouse as set forth in claim 1, wherein the mouse is a strain of *Mus musculus*.

3. The transgenic mouse as set forth in claim 1, wherein the α1G gene of the mouse has a deletion of an exon encoding amino acid residues 82-118 at N-terminal.

4. A method of preparing the transgenic mouse of claim 1 comprising:
   (1) inserting a targeting vector of an α1G gene into mouse embryonic stem cells;
   (2) obtaining a chimera mouse by injecting the mouse embryonic stem cells into the blastocoele of a blastula;
   (3) obtaining a α1G +/− heterozygote mouse by mating the chimera mouse and a wild-type mouse; and
   (4) obtaining the α1G −/− homozygote by mating a female 1G +/− heterozygote mouse and a male 1G +/− heterozygote mouse.

5. The method as set forth in claim 4, wherein the targeting vector comprises a PGK-neo cassette.

6. The method as set forth in claim 4, wherein the targeting vector further comprises α1G homologous fragments and a thymidine kinase gene cassette located at 3'-end.

7. A method for screening an agent for treating absence seizure using the transgenic mouse of claim 1 comprising:

(a) administering an absence seizure-inducing agent to a group of wild type mice and a group of the transgenic mice of claim 1;
(b) administering drug candidates to the group of the wild type mice and the group of transgenic mice of step a;
(c) comparing electrophysiological or behavioral traits with respect to absence seizure of the group of wild type mice and the group of the transgenic mice of step b; and
(d) selecting a drug candidate which alleviates the electrophysiological or behavioral traits of the group of wild type mice on a level with those of the transgenic mice.

8. The method as set forth in claim 7, wherein the absence seizure-inducing agent is (RS)-baclofen or γ-butyrolactone.

9. The method as set forth in claim 7, wherein the electrophysiological trait is a burst-mode firing, spike-and-wave discharges (SWDs), or intra-thalamic SWDs.

10. The method as set forth in claim 7, wherein the behavioral trait is selected from the group consisting of:
i) mild tremors of the head;
ii) whole body tremors with loss of postural control;
iii) erratic running, erratic jumping, or tonic-clonic movement of the limbs; and
iv tonic extension of the whole body or death.

* * * * *